(12) United States Patent
Kuepper et al.

(10) Patent No.: US 8,568,972 B2
(45) Date of Patent: Oct. 29, 2013

(54) SUBSTANCES CAUSING DIFFERENTIATION (75) Inventors: Jan-Heiner Kuepper, Kusterdingen (DE); Reinhard Kandolf, Hechingen (DE); Ralph Meyer, Waldbockelheim (DE)

(73) Assignee: Medicyte GmbH, Heidelberg (DE)

( * ) Notice: Subject to any disclaimer, the term of this patent is extended or adjusted under 35 U.S.C. 154(b) by 30 days.

(21) Appl. No.: 12/498,300

(22) Filed: Jul. 6, 2009

(65) Prior Publication Data

US 2009/0291429 A1 Nov. 26, 2009

Related U.S. Application Data (63) Continuation of application No. 11/495,182, filed on Jul. 27, 2006, now abandoned, which is a continuation of application No. 10/431,705, filed on May 8, 2003, now abandoned, which is a continuation of application No. PCT/EP01/12660, filed on Oct. 31, 2001.

(30) Foreign Application Priority Data

Nov. 11, 2000 (DE) .................................. 10 056 059

(51) Int. Cl.
*C12Q 1/68* (2006.01)
*C12P 21/04* (2006.01)
*C12N 15/00* (2006.01)
*C12N 5/00* (2006.01)
*C07H 21/04* (2006.01)

(52) U.S. Cl.
USPC ......... 435/6.1; 435/6.11; 435/69.1; 435/70.1; 435/320.1; 435/325; 536/24.1

(58) Field of Classification Search
None
See application file for complete search history.

(56) References Cited

FOREIGN PATENT DOCUMENTS

WO    WO 98/44141    10/1998

OTHER PUBLICATIONS

Lybarger et al (Cytometry 25:211-220, 1996).*
Primig et al (Gene 215: 181-189, 1998).*
Oh et al (Mol. Cells 11(2): 192-197, 2001).*
Yamaguchi et al (NeuroReport 1(9): 1991-1996, 2000).*
Wang et al (Anim. Biotech. 12(2): 101-110, 2001).*
Biard et al (Cancer Res. 52: 5213-5218, 1992).*
Komura et al (Biochim. Biophys. Acta (1260(1): 73-78, 1995).*
Biard, D., et al. (1992) "Flow Cytometric Detection of Drugs Altering the DNA Methylation Pattern" Cancer Res. 52:5213-5218.
Collas, P. (1998) "Modulation of plasmid DNA methylation and expression in zebrafish embryos" Nucleic Acids Research 26:4454-4461.
Database (1999) "Development of a Transgenic Model to Assess Bioavailable Genotoxicity in Sediments" LEDO, Accession No. XP002193932.
Database (2000) "pHygEGFP" Clontech Catalog #6014-1, Accession No. XP00293931.
Grassi, G. et al. (2003) "Inhibitors of DNA methylation and histone deacetylation activate cytomegalovirus promoter-controlled reporter gene expression in human glioblastoma cell line U87" Carcinogenesis 24:1625-1635.
Inouye L. et al. (1999) "Development of a transgenic model to assess bioavailable genotoxicity in sediments" Dredging Research Technical Note EEDP-01-43.
Imahori, K. et al. (1998) "Biochemistry Dictionary", vol. 3, Tokyo Kagaku Dojin Co., Ltd. p. 1454.
Liu, L., et al. (2001) "In vivo gene repair of point and frameshift mutations directed by chimeric RNA/DNA oligonucleotides and modified single-stranded oligonucleotides" Nucleic Acids Res. 29(20):4238-4250.
Lybarger, L. et al. (1996) "Rapid generation and flow cytometric analysis of stable GFP-expressing cells" Cytometry 25:211-220.
Oh, S-C. et al. "Generation of fusion genes carrying drug resistance, green fluorescent protein, and herpes simplex virus thymidine kinase genes in a single cistron" Mol. Cells 11:192-197, (2001).
Primig, M., et al. (1998) "A novel GFPneo vector designed for the isolation and analysis of enhancer elements in transfected mammalian cells" Gene 215:181-189.
Stull R.A. et al., (2000) "Simultaneous Flow Cytometric Analyses of Enhanced Green and Yellow Fluorescent Proteins and Cell Surface Antigens in Doubly Transduced Immature Hematopoietic Cell Populations", Cytometry 40:126-234.
Wang, H.J. et al. (2001) "Expression of porcine growth hormone gene in transgenic rabbits as reported by green fluorescent protein" Animal Biotechnol. 12:101-110.
Yamaguchi, M. et al. (2000) "Visualization of neurogenesis in the central nervous system using nestin promoter-GFP transgenic mice" Develop. Neuroscience 11:1991-1996.

* cited by examiner

*Primary Examiner* — Richard Schnizer
(74) *Attorney, Agent, or Firm* — Knobbe, Martens, Olson & Bear, LLP (57) ABSTRACT

A DNA construct is described which contains a fusion gene under the control of a promoter. The fusion gene comprises at least one resistance gene and at least one reporter gene and is slightly toxic to a host cell transfected with that DNA construct. That DNA construct can be encoded on a plasmid or a virus. Further, a method is described for using the DNA construct to identify substances that may cause a differentiation in eukaryotic cells.

13 Claims, 7 Drawing Sheets

Fig. 1

| Untreated | 0.5 μM Aza |
|---|---|
|  |  |
| 100 nM TSA | 2.5 μM Aza |
|  |  |
| 1 μM TSA | 20 μM Aza |
|  |  |

SUBSTANCES CAUSING DIFFERENTIATION

CROSS REFERENCES TO RELATED APPLICATIONS

This application is a continuation of U.S. application Ser. No. 11/495,182, filed Jul. 27, 2006, which is a continuation of U.S. application Ser. No. 10/431,705, filed May 8, 2003, which is continuation of International Patent Application PCT/EP01/12660 filed on Oct. 31, 2001, designating the U.S., and published in German, which claims priority of German patent application DE 100 56 059.8 filed on Nov. 11, 2000, all which are incorporated herein by reference in their entireties.

BACKGROUND OF THE INVENTION

1. Field of the Invention

The present invention relates to a method for identifying substances causing differentiation in eukaryotic cells, to DNA constructs, plasmids, viruses and cell lines used in said method, and to a method of preparing a pharmaceutical composition.

2. Description of the Related Art

Differentiation of cells from stem cells is a general biological phenomenon during embryonic development, but also plays a very large part in regeneration processes in the adult organism (e.g., skin regeneration, formation of blood, regeneration of intestinal epithelia, liver regeneration after poisoning or alcohol abuse, etc.). As in all important biological processes, disruptions may cause chronic diseases or may be lethal.

During tumorigenesis, there is very frequently, if not always, a "back"-differentiation of cells, i.e. cells revert to an undifferentiated, embryonic state. Despite great improvements in the methods for early diagnosis and therapy of tumor diseases, mortality is still very high and affected patients suffer immensely. Therefore, finding and developing novel and more effective cancer medicaments (cytostatics) is of extraordinary importance for health policy and have, from the perspective of the pharmaceutical industry, a very large growth potential on the drugs market.

Since many genetic modifications occur on the path from a normal healthy cell to a tumor cell, there are in principle also many possibilities of interfering with the metabolism of tumor cells and thus preventing growth and dissemination. Thus, the largest class of cytostatics leads to damage of cellular DNA. After cell division, this causes lethal mutations, or the cell dies as a direct result of the triggering of the so-called programmed cell death (apoptosis). This affects all rapidly growing cells, i.e. not only tumor cells but also healthy growing cells.

Another class of cytostatics is that of the antimetabolites which halt the metabolism of rapidly growing cells. A third class of cytostatics damages the so-called spindle fiber apparatus of dividing cells, thereby inhibiting cell division or killing the cells directly. A fourth and relatively new class is that of anti-angiogenetic substances which interfere with the ability of tumor cells to induce new blood vessels for their own supply.

A relatively new class of cytostatics, which is relevant in context with the present invention, interferes with the expression pattern of genes which have been partly switched off during tumorigenesis. These are frequently so-called tumor suppressor genes and differentiation genes. The renewed induction and expression of said genes usually leads to a loss of growth advantages of a cancer cell and may also make it easier for the immune system to attack said cell.

The fact that such differentiation-causing substances interfere with the state of methylation of so-called "CpG is-lands" has been known for a long time. CpG islands are found particularly frequently in the 5'-regulatory sequences of genes and play an important part in genomic imprinting, i.e. in regulating paternal versus maternal gene expression. It is possible to switch off genes by methylating the CpG islands present in promoters. If the DNA methylase mainly responsible for methylation is inactive, lethal disruptions in development occur, as can be shown in a knockout model in mice.

It is therefore assumed nowadays that there is a genetically controlled equilibrium of methylation and demethylation in embryogenesis. A disruption of this equilibrium is often present in tumor cells. Thus, it has been found that it is possible to switch off promoters of tumor suppressor genes by methylation of the CpG islands, which is why, for example, the hypomethylation-inducing substance 5'-azacytidine (Aza) acts as a potent cytostatic agent in many types of tumor.

Another mechanism important for differentiation is the influence of histone acetylation. Histones are DNA-binding proteins which can regulate chromatin structure and also influence gene expression. This takes place preferably via biochemical modifications of said histones, for example by acetylation or phosphorylation. Thus, the substance trichostatin A (TSA) is known as a specific inhibitor of histone deacetylase. Recently, it was shown that deacylation of histone H4 leads to chromatin condensation and thereby can suppress gene expression. Accordingly, inhibition of histone deacetylase by TSA leads to chromatin decondensation and can thereby remove suppression of gene expression.

It must be assumed that there are still many other, as yet unknown mechanisms which can be used by tumor cells to switch off expression of differentiation genes and tumor suppressor genes dangerous to them.

While for some classes of cytostatics there are already very good assay systems which also can be used to identify novel compounds, there is, however, a lack of methods for identifying, as mentioned above, such substances capable of causing differentiation. However, this novel class of cytostatics is particularly interesting, because it has great potential for controlling tumors and is associated with substantially fewer side effects than the traditional cytostatics.

The following widespread in vitro test systems are available for identifying substances which cause DNA damage and could therefore potentially be used as cytostatics: the Ames test, or else *Salmonella typhimurium* test (STY), is based on the mutagenicity of substances in bacteria, while the SOS-Chromotest is based on inducing the bacterial SOS system by genotoxic agents. Both tests have comparable sensitivities, but have the fundamental disadvantage that genotoxic action of substances can vary in bacteria and higher organisms.

For this reason, the Micronucleus test, the single cell gel test (SCG test), also known as comet assay, and the test for sister chromosome exchange (SCE test), which are based on eukaryotic cell systems, have been developed. In the literature, a cell line, A4/4, which contains a lacZ gene under the control of the heavy metal-inducible metallothionein promoter has been described. The authors report that the promoter is switched off during cultivation but can be induced again by the demethylating substance 5'-azacytidine (Biard et al. 1992 *Cancer Res* 52:5213-5218).

The previously known assay systems for identifying DNA-damaging agents, however, are not suited to identify substances causing differentiation, since the mechanism is completely different.

The reporter cell line described by Biard et al. has the decisive disadvantage of being an inducible system. The demethylating action of substances can be visualized only if the inducer for the promoter is used at the same time. The authors have chosen the metallothionein promoter which is induced by heavy metals such as cadmium and zinc. There are hundreds of indications in the literature for heavy metals themselves inducing gene expression. As a result, the gene expression-causing action of the heavy metals required for the system superimposes the demethylating action of some substances, i.e. unspecific, false negative or false positive results are very easily possible. The cell line was prepared for the purpose of being able to find demethylating substances. These substances may cause differentiation but are, as explained above, not the only substances capable thereof. Since there are, after 1992, no further publications regarding this cell line, it is neither known whether this cell line is stable nor whether it is suitable for detecting other differentiation processes as well.

SUMMARY OF THE INVENTION

In view of the above, it is an object of the present invention to provide a method of the type mentioned at the beginning, which can be used to identify in a rapid, simple and reliable manner substances causing differentiation, and auxiliary substances which can be used in said method.

This object is achieved by a DNA construct which comprises a fusion gene under the control of a promoter, wherein said fusion gene comprises at least one resistance gene and at least one reporter gene and is slightly toxic to a host cell transfected with said DNA construct so that said promoter is switched off when expression of the resistance gene is not required for growth of the transfected host cells, since, for example, the nutrient medium lacks the appropriate antibiotic.

Further objects of the invention are a plasmid having such a DNA construct, a virus having an expression cassette containing said DNA construct or coding therefor, i.e. a DNA virus or a retrovirus, and a eukaryotic cell, in particular human cell, which is stably transfected with said plasmid or infected with said virus, in particular the cell line U87-HGFP which was deposited in accordance with the Budapest Treaty at the DSMZ in Braunschweig, Germany, under deposition number DSMZ ACC 2473 on Nov. 9, 2000, and a method of using said DNA construct and/or said plasmid and/or said virus and/or said cell for identifying substances which cause differentiation in eukaryotic cells.

A further object is a method for identifying substances which are capable of causing differentiation in eukaryotic cells, comprising the steps:
  a) incubating the novel cells in a culture medium containing a selection substance corresponding to the resistance gene,
  b) inoculating a culture medium lacking said selection sub-stance with the incubated cells from step a) and incubating the inoculated cells for approx. 5 to approx. 100, preferably approx. 24, hours,
  c) adding a substance to be identified to said culture medium of the cells from step b) and incubating further for approx. 1 to approx. 5, preferably approx. 2, days, and
  d) checking the incubated cells from step c) for increased reporter gene expression compared to cells from step b).

The present invention completely solves the problem of identifying substances causing differentiation.

In this connection, preference is given to selecting the promoter from CMV promoter, RSV promoter, cellular promoters of tumor suppressor genes and promoters of differentiation genes, to selecting the reporter gene from GFP, LacZ, luciferase, to selecting the resistance gene from hygromycin gene, neomycin gene, puromycin gene, and/or to the fusion gene containing at least one gene coding for a polypeptide capable of developing an action toxic to the host cell, such as, for example, GFP, which itself is slightly toxic or cytosine deaminase or thymidine kinase which convert the prodrugs 5'-fluorocytosine and ganciclovir, respectively, into toxic substances.

The cell line also includes a fusion gene under the control of the human cytomegalovirus promoter (CMV promoter). This promoter is usually extremely strong in cells and therefore need not be induced, in contrast to the metallothionein promoter of the prior art. Moreover, it is known that the promoter can be switched off under certain conditions, in particular in vivo.

The fusion gene here consists of the resistance gene for the antibiotic hygromycin (hygro) and green fluorescent protein (GFP). Transfection of the glioblastoma cell line U87 with this construct generated the cell line U87-HGFP, after selection using the antibiotic hygromycin. This cell line expresses the fusion gene in the presence of the antibiotic, this being very clearly visible in fluorescence microscopy on the basis of GFP fluorescence. If the antibiotic is removed for just a few days, the cell downregulates the CMV promoter, since the fusion protein is slightly toxic to the cells. As the inventors observed, the said fusion protein accumulates in particular cell compartments (probably the ER). Treating said cells with the differentiation-causing substances 5'-azacytidine and/or trichostatin A at very low concentrations results in very strong upregulation of the CMV promoter, visible due to increased GFP fluorescence, within just two days.

Up until now, no cell line has been described or known in which substances causing differentiation can be detected using an expression unit consisting of CMV promoter and hygromycin-GFP fusion. The system is very reliable, with the presence of hygromycin during routine cultivation of the cell line preventing the loss of said expression unit. The cell line has the intrinsic capability of virtually completely downregulating the CMV promoter only a few days after removing hygromycin. The promoter is upregulated again when adding substances causing differentiation.

The advantage compared to the known system is, inter alia, the use of a fusion gene which combines a plurality of properties: (I) positive selectability by the hygromycin gene, i.e. the expression unit is retained in a stable manner when adding the antibiotic; (II) negative selectability, i.e. in the absence of hygromycin B the toxic effect of the GFP gene selects for cells in which the promoter is switched off; (III) identifiability due to intrinsic fluorescence of GFP. These properties render the system very stable and reliable.

The system needs no inducer except the differentiation substance to be tested and is therefore unaffected by disruptions or superpositions by an inducer.

The system has proved to be capable of finding not only demethylation but also histone acetylation.

Using the GFP as reporter, it is possible to observe the promoter activity, and thus the action of substances causing differentiation, both in living cells and in fixed cells (fluorescence microscopy) and to quantify it exactly and reproducibly by means of flow cytometry.

According to another object, it is also possible in the novel method to use other reporter expression units consisting of a promoter (CMV promoter, RSV promoter, cellular promoters of tumor suppressor genes or differentiation genes), a selection marker (hygromycin gene, neomycin gene, puromycin gene, etc.) fused to a reporter (GFP, LacZ, luciferase), and a "toxic" gene (e.g. GFP, cytosine deaminase, HSV thymidine kinase).

Cytosine deaminase or thymidine kinase would then additionally need toxic but not lethal concentrations of the pro-drugs 5'-fluorocytosine and ganciclovir, respectively. This would select for cells which down-regulate the promoter.

These constructs may also be transfected in cell lines other than U87, or the studies may also be carried out in vivo, i.e. on transgenic animals.

The cell line U87-HGFP, which is still a further object of the invention, has a particular advantage in that the promoter can be switched off within a short time and reliably. Furthermore, the method can be automated, making it possible to screen many substances in a short time.

The cell line has the further advantage of being a tumor cell line so that the substances are searched for in a cancer cell which is thus not only a model system but also, at the same time, a test system. Another advantage is the fact that these cells differentiate with addition of the appropriate substances, and this can be seen due to the change in morphology.

A substance identified in this way is thus not only capable of reactivating a downregulated promoter but can also force a cancer cell to differentiate and is thus a potential cytostatic.

Against this background as another object, the invention also relates to a method of using a substance identified by the novel method for preparing a pharmaceutical composition for treating malignant and benign tumor diseases, and to a method for preparing a pharmaceutical composition, which comprises the novel method and mixing the identified substance with a pharmaceutically acceptable carrier.

Further advantages arise from the description and the attached drawings.

It is obvious that the features mentioned above and still to be illustrated below can be used not only in the combinations indicated in each case but also in other combinations or on their own, without leaving the scope of the present invention.

BRIEF DESCRIPTION OF THE DRAWINGS

FIG. 3 (A) shows U87 parent line and H-GFP, treated with different final concentrations of 5-azacytidine for 48 h. U87H-GFP shows a two-fold increase in the fluorescence intensity mean value already at 2.5 µM Aza (compared to untreated cells). This reporter cell line attains a three-fold increase when 20 µM Aza are used. We obtain an approximately two-fold increase in the fluorescence intensity mean value of U87 parents only at the highest concentration used.

FIG. 3 (B) shows the increase in H-GFP gene expression due to trichostatin A. Approximately 10$^5$ cells of each cell line were cultured with different final concentrations of trichostatin A for 48 h. As the histogram shows, we obtained a three-fold and four-fold increase in the fluorescence intensity mean value when using a final concentration of 1 µM and 3 µM TSA in U87H-GFP (compared to untreated cells). In both histograms, all mean values, standard deviations and P values are derived from at least five different values (n=5) obtained from two different independent experiments. All P values refer to untreated cells.

FIG. 3 (C) shows treatment with two different combinations of 5-azacytidine and trichostatin A. The two cell lines (10$^5$ cells/well) were cultured in the presence of two different combinations of Aza and TSA for 48 h. In both cases, a three-fold increase in the fluorescence intensity mean value is observed in U87H-GFP (compared to untreated cells). However, the difference is not significant (p=0.09) when we compare the increase for U87H-GFP which has been treated with the two different medicament combinations.

FIG. 3 (D) shows trichostatin A and 5-azacytidine, in each case individually and in combination. 10$^5$ cells of the U87H-GFP cell line were treated with 200 nM TSA, 1 µM Aza and with the combination of both for 48 h. When using the two medicaments in each case individually, we obtained an approximately two-fold increase in the fluorescence intensity mean value (P~10$^{-9}$ and <10$^{-4}$, compared to untreated cells). When using the combination of the two medicaments, we obtained a small and significant increase in the fluorescence intensity compared with each medicament alone (P~0.02). The mean values, standard deviations and P-values are based on ten values (n=10) which were obtained in two independent experiments.

[I and IV] show dot plots referred to DNA staining of treated and untreated cells. In order to exactly define a population of (2N+4N) nuclei, a region (R1) was utilized. [II and V] show dot plots referred to BrdU incorporation into DNA. The values 200 and 400 on the linear scale of FL3-A fluorescence correspond to the amount of 2N and 4N DNA in the nuclei. All events shown correspond to the R1 region. [III and VI] show an isotype control for establishing the quadrants for the dot plots of BrdU incorporation. The anti-isotype antibody represents nonspecific binding and was used as a negative control for the anti-BrdU antibody. The percentages of cells in different phases of the cell cycle were determined using the dot plots of BrdU incorporation (in quadrant: bottom left region=G1-G0; bottom right region=G2; top left region=S; top right region=M).

DETAILED DESCRIPTION OF THE PREFERRED EMBODIMENT

1) Cloning of pCMV-HygroEGFP
Intermediate Plasmid 1 Called pScriptpolyA (3595 bp).

Starting plasmid pCRScript SK(+) AmpR+ cut with EcoRV and HindIII, and subsequent ligation with SmaI/HindIII fragment which contains a 625 bp HSV thymidine kinase polyadenylation signal from pTKneo (blunt end ligation).
Intermediate 2: pCMVA (4260 bp).

Insertion of a 670 bp hCMV promoter fragment from pL15Tk [cut with PstI, blunt-ended using T4 DNA polymerase] into intermediate 1, pScriptpolyA, cut with SrfI (blunt end ligation).
Intermediate 3: pCMV-EGFP (4975 bp).

Ligating of the EGFP reading frame from plasmid pEGFP (Clontech) cut with BamHI/NotI (end filled in using Klenow polymerase) into vector pCMVA opened with PstI (intermediate 2, blunt-ended using T4 DNA polymerase) (blunt end ligation).
Final pCMV-HygroEGFP (6052 bp).

Ligation of a 1026 bp PCR fragment containing the open reading frame of the hygromycin resistance gene from pTkHygro (Stopcodon removed by said PCR) into AgeI-opened vector pCMV-EGFP (blunt-ended by filling in ends using Klenow polymerase) (blunt end ligation).

Figure 5:
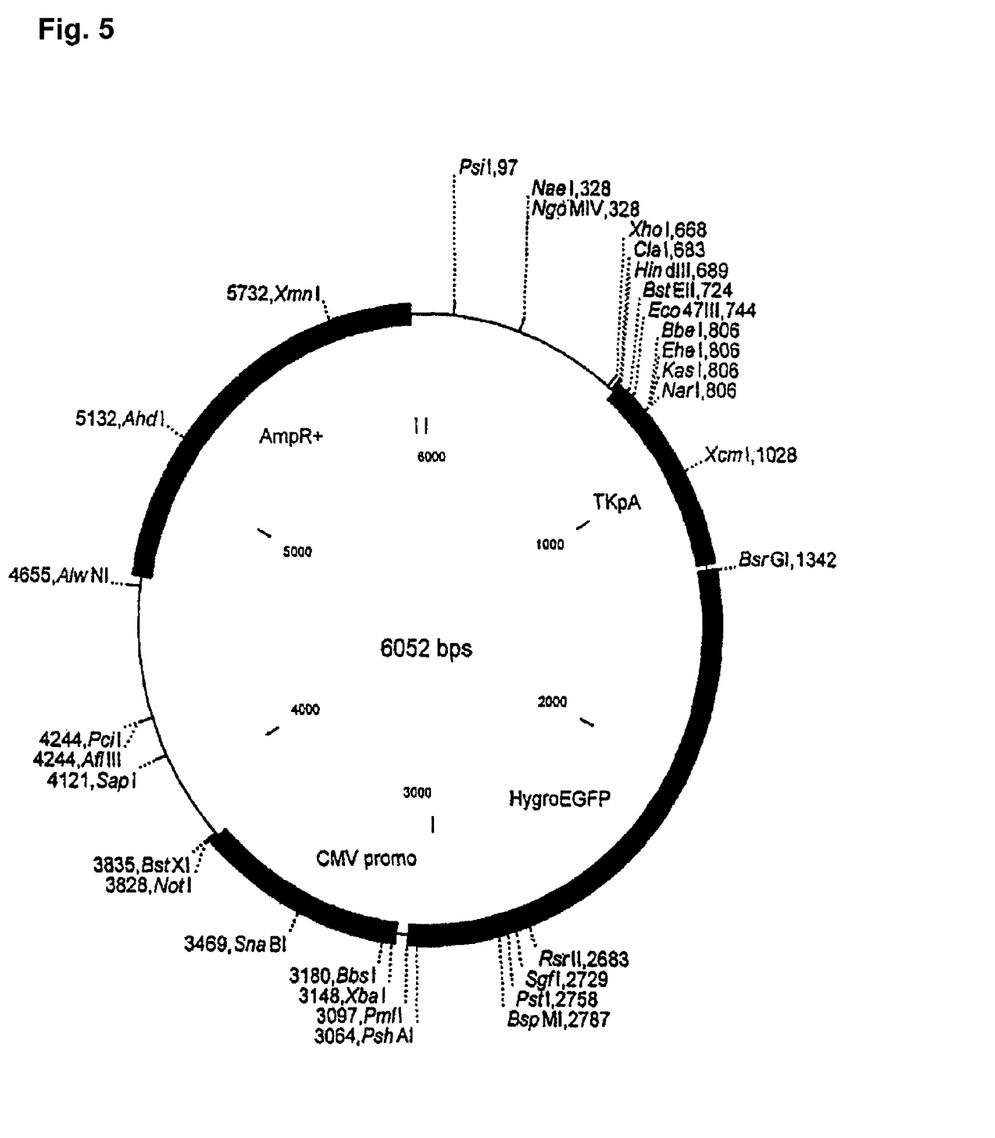
FIG. 5 shows plasmid pCMV-HygroEGFP which was used in the experiments.

The plasmid is depicted in FIG. 5.

2) Materials and Methods
Cell Lines

U87H-GFP is a cell line derived from the human glioblastoma cell line U87 after stable transfection with plasmid pCMV-hygroEGFP. This plasmid which is integrated into the genomic DNA is derived from PCR-Script™ (Stratagene) and carries a fusion gene downstream of the human CMV promoter. This fusion gene contains the gene for resistance to hygromycin, which is linked to the gene coding for the enhanced green fluorescent protein (EGFP). The resulting gene (called H-GFP) codes for a protein which imparts resistance to hygromycin B and which can be readily detected by fluorescence microscopy and flow cytometry analysis. In contrast, the parent cell line U87 does not contain any plasmid and can be used as a negative control.

U87H-GFP and the parent line U87 were cultured in Dulbecco's Modified Eagle's Medium, (D-MEM, low glucose, Gibco, BRL) supplemented with 10% fetal calf serum (Seromed), 100 units/ml penicillin, 100 µg/ml streptomycin and 1 µg/ml amphotericine B (Gibco, BRL) at 37° C. in a humidified atmosphere containing 5% $CO_2$. For the U87H-GFP cell line, the culture medium was supplemented with 600 units/ml hygromycin B (Calbiochem).

U87H-GFP and the parent cells were seeded at $1-2\times10^5$ cells/well on 6-well plates (Nuclon, NUNC), using D-MEM without hygromycin B, and incubated for adhesion for 24 h. This was followed by adding 5-azacytidine and trichostatin A (Sigma Chemicals, Co.) at different final concentrations (2.5-5-10-20-40 µM for Aza; from 10 nM to 3 µM for TSA) to the culture medium. After two days of treatment, fluorescence microscopy and flow cytometry analyses were carried out.

Fluorescence Microscopy

Figure 1:
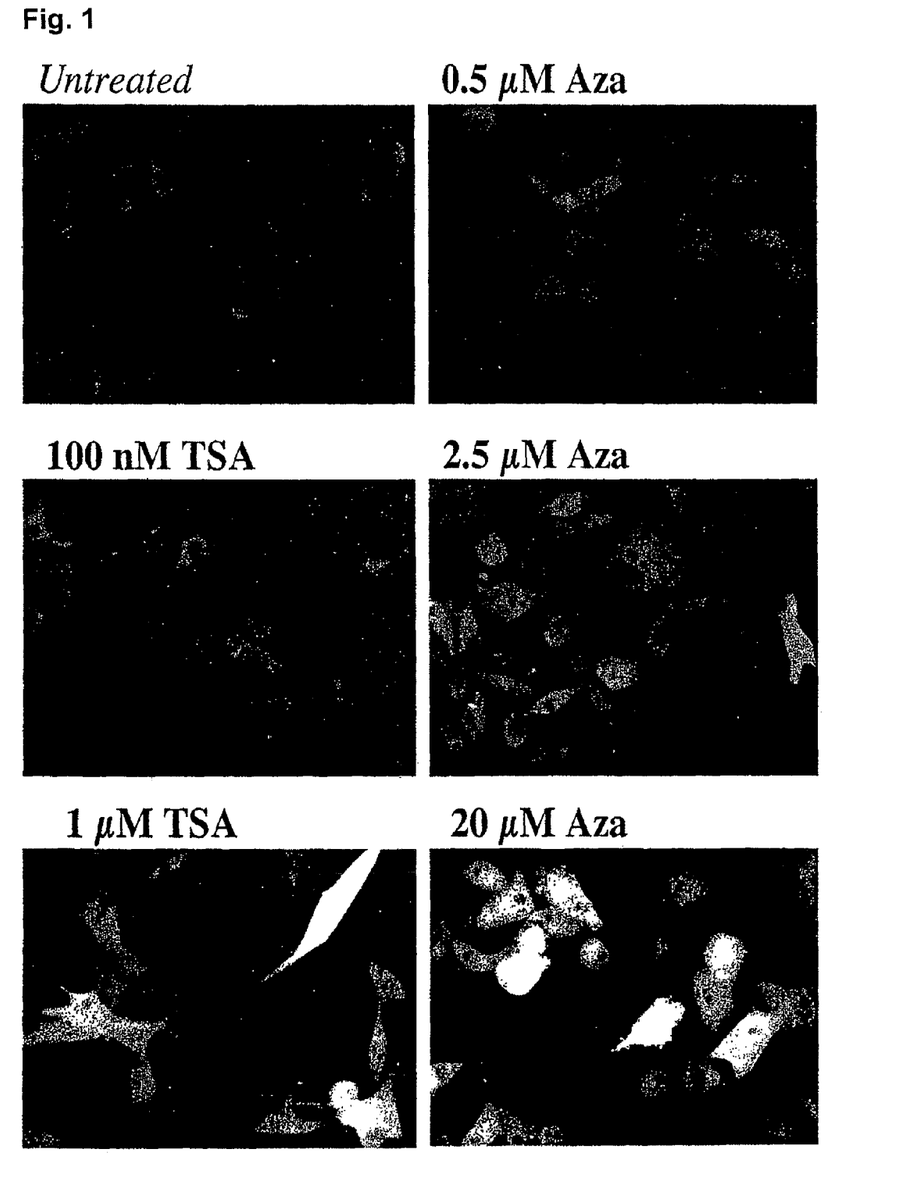
FIG. 1 shows detection of H-GFP gene amplification by 5'-azacytidine and trichostatin A by means of fluorescence microscopy: U87H-GFP cells, growing on coverslips, were treated with 5-azacytidine (0.5-2.5-20 µM) and trichostatin A (0.1-1 µM) for 48 h. Owing to amplification of the H-GFP gene, an increasing green fluorescence signal was observed when comparing untreated with treated cells. The parent cells had no signal sufficiently strong for observation by fluorescence microscopy (data not shown). All images correspond to a magnification of 400×.

Approximately $10^5$ cells of each cell line were seeded on polylysine-coated coverslips, treated with different concentrations of Aza and TSA for 48 h and then fixed in 5% formaldehyde at room temperature for 30 min. This was followed by analyzing all samples under a fluorescence microscope (Axiophot, Zeiss, Germany) and recording various images which correspond to the different final concentrations of each medicament (FIG. 1).

Flow Cytometry Analyses of Cells Expressing the Hygromycin-EGFP Fusion Gene.

In order to prepare samples for FACS analysis, cells were incubated in the 6-well plates in 0.05% trypsin containing 0.5 mM EDTA (Gibco, BRL) at 37° C. for 5 min, followed by stopping the trypsin action by adding two volumes of culture medium. The cells were harvested, centrifuged at 500×g for 5 min and resuspended in 1 ml complete D-MEM. In order to stain dead cells, propidium iodide (final concentration 10 µg/ml) was added to each sample. The cells were then again centrifuged and resuspended in phosphate-buffered saline (PBS 1×, pH 7.4), before analyzing them by means of FACS.

The cells were analyzed using FACScalibur (Becton Dickinson) with the flow rate corresponding to approximately 500 events/s.

In order to exactly define a cell population and to exclude cell debris and aggregates, a region of interest was established on the dot plot (FSC compared to SSC). In the two-parameter histogram of propidium iodide, dead cells were distinguished by comparison to forward angle light scatter (FSC). The fluorescence intensity of individual cells was measured on a logarithmic scale, each logarithmic histogram representing $2\times10^4$ counted events. The fluorescence intensity mean value (MFI) was the parameter used for defining the increase in the fluorescence intensity in each cell population.

Cell Cycle Analysis

U87H-GFP and the parent cells were seeded at $5\times10^3/cm^2$ in T25 flasks (Nuclon, NUNC), using D-MEM without hygromycin B for both cell lines. Half of the flasks were treated with 5 µM Aza and the other, as a negative control, without any medicaments. After 42 h, BrdU was added to the medium (final concentration of 10 µM), and 6 h later the cells were prepared for cell cycle analysis.

The cells were harvested, centrifuged at 500×g for 5 min and fixed in chilled 70% strength ethanol for 20 min. BrdU incorporation into the DNA was detected by using $3\times10^5$ cells of each Aza-treated or untreated cell line.

PBS 1×/0.5% BSA (washing buffer) was added, and the cells were centrifuged at 500×g for 5 min. The pellet was then resuspended in a denaturing solution (HCl 1M, PBS 0.5× BSA 0.5%) and washed again after 20 min. This was followed by re-suspending the pellet in 0.1M sodium borate ($Na_2B_4O_7$), pH 8.5, for 2 min and then adding the washing buffer. After this passage, the total volume of each sample was divided into two halves (one half being used for the isotype antibody, the other one for the BrdU antibody), centrifuged at 500×g for 5 min, resuspended in the buffer containing the anti-isotype or anti-BrdU monoclonal antibodies (Becton Dickinson) and, after 30 min, washed with PBS 1×/0.5% BSA. The supernatant was discarded and the pellet resuspended in RNAse A (final concentration 100 µg/ml); the DNA was stained by also adding to the solution 7-AAD (Via-PROBE, Becton Dickinson). After 1 h (in the dark), the samples were washed and then resuspended in PBS 1×/0.5% BSA. DNA fluorescence of the nuclei (approximately $10^4$ nuclei were analyzed for each cell population) was measured by means of the abovementioned FACScan flow cytometer (Becton Dickinson) and the percentages of cells in the G0 and G1, S, G2 and M phases of the cell cycle were analyzed on the basis of the FACScan software programs.

3) Results

The cell line U87H-GFP contains the plasmid pCMV-hygroEGFP in which activation of the hCMV promoter is usually regulated at a low level. Said plasmid imparts to the cell line resistance to hygromycin B and a basic green fluorescence compared to the parent cell line. The hCMV promoter was shown as being completely repressed by methylation of the 5'-CpG site of cytosine (Prosh S. et al. 1996 Biol Chem Hoppe Seyler 377(3):195-201). In order to estimate the property of the promoter of being able to be activated by medicaments interfering with the DNA methylation state and chromatin condensation, U87H-GFP and the parent line U87 were kept in the presence of Aza and TSA for several days. Prior to the experiment, hygromycin B was removed from the medium in order to obtain a decrease in basic activation of the hCMV promoter and furthermore to detect promoter activation by Aza and TSA.

FIG. 1 shows fluorescence microscopy images of U87H-GFP cells treated with different final concentrations of Aza (0.5-2.5-20 μM) and TSA (100 nM, 1 μM) for 48 h. Comparison of basic expression of the reporter cell line (untreated cells) with those samples treated with different final concentrations of Aza and TSA makes it possible to detect an increase in H-GFP gene expression in the images. At 20 μM Aza and 1 μM TSA, the increase in the green fluorescent signal is clearly defined. Parent cells show a weak increase in basic green fluorescence, which was detectable only by FACS analysis and not by fluorescence microscopy.

Furthermore, a change in the morphology of the cells was observed at high concentrations of TSA and Aza, indicating that these substances may force the tumor cells U87 back into differentiation.

Figure 2:
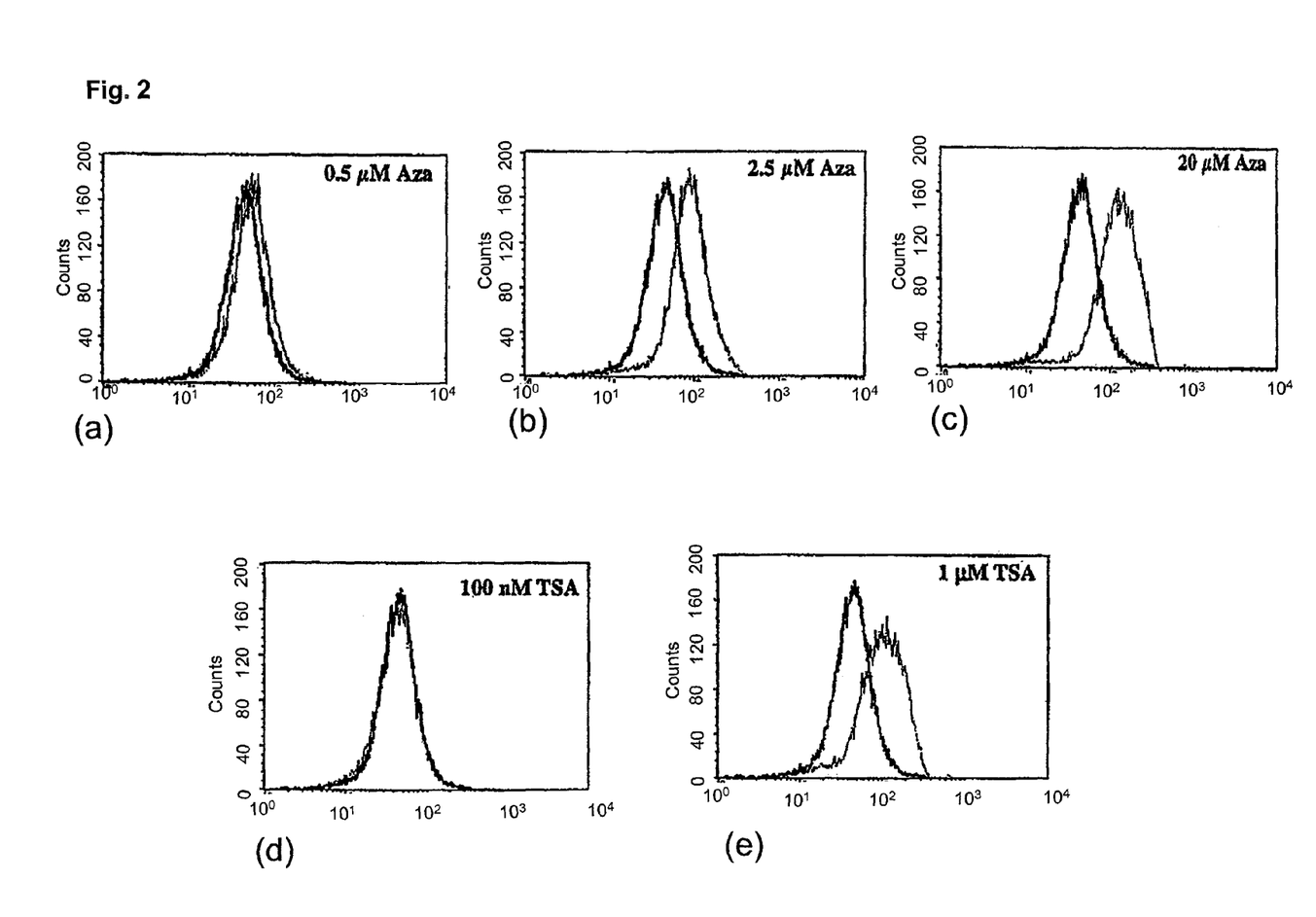
FIG. 2 shows FACS fluorescence profiles, with U87 H-GFP and parent cells obtained after treatment for 48 h using different concentrations of 5-azacytidine and trichostatin A: 1-2×10$^5$ cells of U87 H-GFP and the parent line were seeded in 6-well plates, treated with 5-azacytidine and trichostatin A for 48 h and then analyzed by flow cytometry as described below. In all histograms, the abscissae correspond to an arbitrary and logarithmic scale which refers to fluorescence intensity, whereas the ordinates refer to the cell number. Each of the curves corresponds to 2×10$^4$ cells counted, and in the overlays, the darker profile corresponds to the untreated cells and the lighter one to the treated cells. Profiles (a) to (e): U87 H-GFP. A shift toward higher fluorescence intensity is clearly visible at 2.5, 20 µM Aza and 1 µM TSA, whereas 0.5 µM Aza and 100 nM TSA curves completely superpose those of the untreated cells. Profiles (f) to (j): U87. Particularly when using 20 µM Aza and 1 µM TSA, a small shift is observed which, however, can be considered as a background increase not caused by the plasmid and cannot be observed by fluorescence microscopy.

FIG. 2 depicts FACS profiles (logarithmic histograms) of samples which were treated with the same concentrations of Aza and TSA as in fluorescence microscopy.

The abscissae correspond to an arbitrary scale which refers to the logarithm of fluorescence intensity, and the ordinates represent the relative cell number. When comparing the control, which had not been treated with the reporter cell line, with the reporter cell line, which had been treated with the abovementioned final concentration, we obtained a shift in the fluorescence profile in the direction of higher intensity. The shift is already clearly visible with additions of 2.5 μM Aza (FIG. 2, profile b) and is well defined at higher concentrations (profile c).

At a final concentration of 100 nM, TSA does not induce in any way an increase in H-GFP gene expression (profile d), but attains a saturation threshold at a final concentration of 1 μM (profile 1). It was not possible to use final TSA concentrations of more than 3 μM, since these proved highly toxic and drastically reduced the number of living cells, as was observed by means of FACS (data not shown).

The parent cell line is likewise sensitive to Aza (FIG. 2, profiles f to h) and TSA (profile i and 1), but the shift in fluorescence intensity is not comparable to those obtained with the reporter cell line and can therefore be explained as a background increase rather than being caused by the plasmid.

Figure 3:
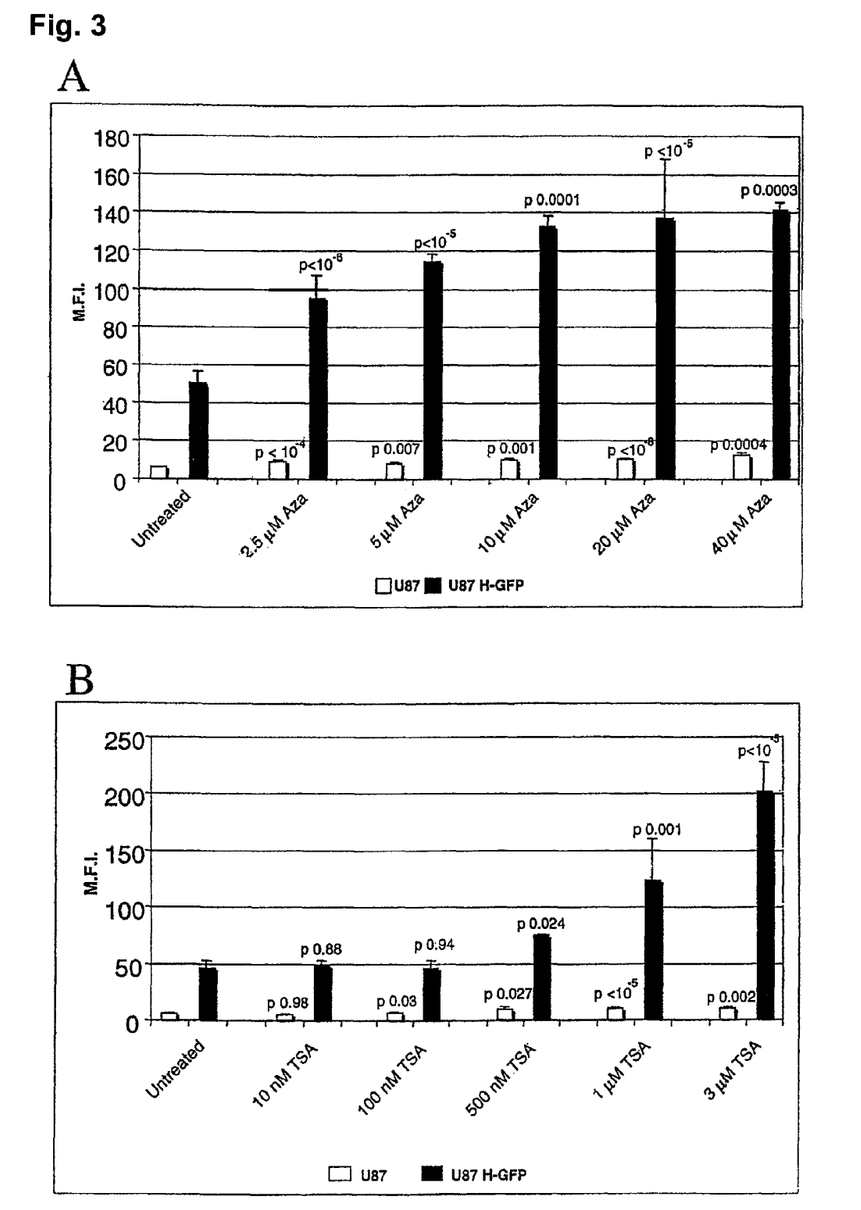

The histogram in FIG. 3A corresponds to the experiment in which the reporter cell line (black bars) and the parent cell line (white bars) were treated with different Aza concentrations for only 48 h. The histogram depicts a two-fold increase in the fluorescence intensity mean value for a comparison of the control (untreated U87H-GFP) with cells treated with 2.5 μM Aza ($P<10^{-6}$, compared to control). When using 20 μM Aza, H-GFP gene expression can achieve a three-fold increase in fluorescence intensity ($P<10^{-5}$, compared to control) A slow increase in basic fluorescence (only by means of FACs analysis and not in fluorescence microscopy) is also visible in the parent cell line (white bars in the histogram), corresponding to less than twice that when using the highest concentration (40 μM Aza). This experiment was also repeated while retaining Aza for 144 h (five days) and with identical final concentrations. We obtained the same shift in the fluorescence intensity average (data not shown).

TSA can also cause amplification of the H-GFP gene, as FIG. 3B reveals. Both cell lines were kept in cultures which different final TSA concentrations for 48 h. The histogram reveals a slight but significant increase in the fluorescence intensity of U87H-GFP for TSA only at 500 nM and not at the lower concentrations used. However, when we used 1 μM and 3 μM TSA, we observed a three-fold and four-fold increase in fluorescence (P=0.001 and $P<10^{-5}$, compared to untreated cells). In the parent cell line, a two-fold increase is visible only for 3 μM TSA.

In order to further investigate whether TSA can act synergistically with Aza, as has been shown for other tumor cell lines (Cameron E. E. et al. 1999 Nat Genet 21:103-107), we used TSA in combination with Aza for 48 h (FIG. 3C) In this experiment, we kept TSA at a fixed final concentration of 1 μM, while changing Aza from 2.5 to 5 μM. In both cases, a three-fold fluorescence increase is observed in U87H-GFP compared to untreated cells, but the difference is not significant when comparing the two combinations of the medicaments (p=0.09). In the next experiment (FIG. 3D) we used TSA and Aza in each case alone and in combination for 48 h. The increase due to the medicaments alone was significant and corresponded to about a two-fold increase, both for 200 nM TSA ($P\sim10^{-9}$, compared to untreated cells) and for 1 μM Aza ($P<10^{-4}$ compared to untreated cells). When we used the combination of the two (200 nM TSA+1 μM Aza), the small increase with respect to the medicaments alone was significant ($P\sim0.02$, compared to the medicaments alone), but the medicaments appeared to act neither in a synergistic nor in an additive way, the reason for this being probably that the increase in fluorescence intensity corresponded to maximum activation of the CMV promoter at these medicament concentrations.

Effects of 5-azacytidine on the Cell Cycle.

Figure 4:
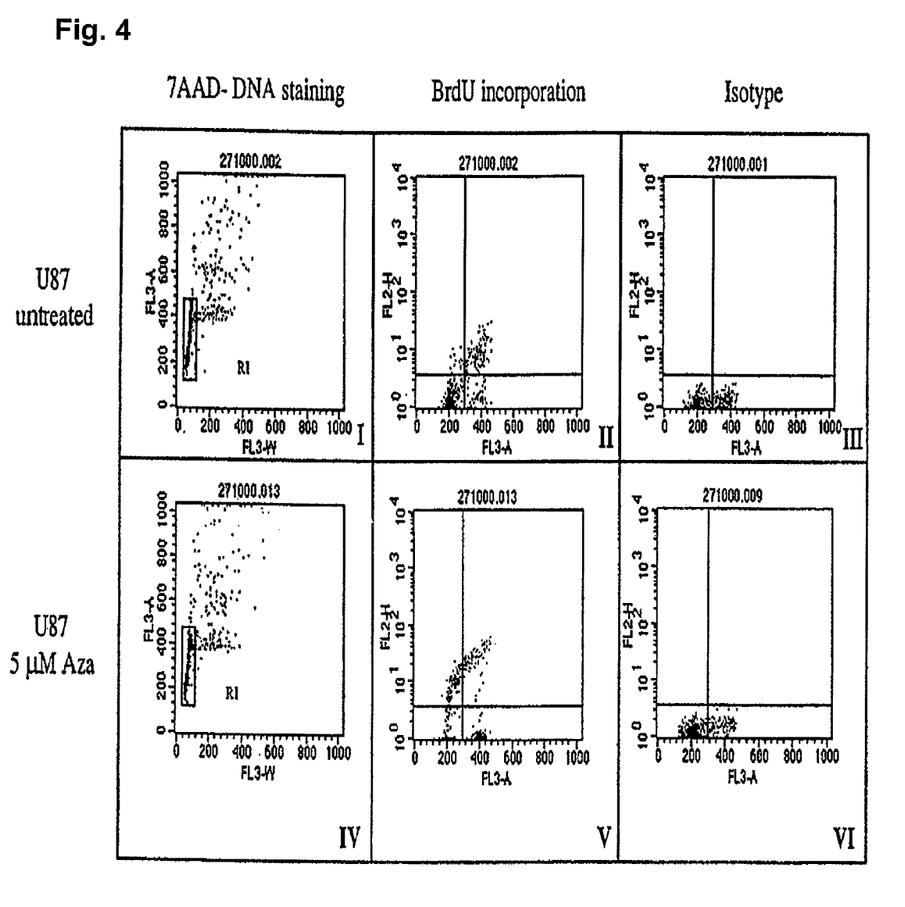
FIG. 4 shows dot plots obtained by FACS analysis of U87H-GFP and the parent line which were either treated or not treated with 5 µM 5-azacytidine for 48 h. Both cell lines were kept in culture in the presence of 5 µM Aza. Two days later, the cell cycles were determined as described. 10,000 cells were analyzed. The procedure for studying the cell cycle by FACS analysis is illustrated below.

U87H-GFP and the parent cells were treated with 5 μM Aza for two days in order to study the effect of cytosine analog on the cell cycle. As FIG. 4 illustrates, the DNA was stained with 7-AAD and in the first two dot plots (I, IV) a single window was utilized (R1) in order to exactly define only one 2N and one 4N nuclei population (corresponds to values 200 and 400 on FL3-A scale). The enclosed population of nuclei was then tested for BrdU incorporation (II, V) by using a PE-conjugated antibody against BrdU. Isotype staining (dot plots III, VI) was used in order to define nonspecific binding of the BrdU antibody and in order to set the quadrant in the BrdU incorporation dot plots. The percentages of the cells in different cell cycle phases were obtained from the dot plots of BrdU incorporation. Table 1 shows the percentages of cells in different cell cycle phases. Azacytidine (at a concentration of 5 μM) has no significant effect on different phases of cells, with the exception of a small increase in the percentage of cells in G2. In contrast, the parent line (U87) appeared to be more sensitive to 5-azacytidine. In this cell line, 5-azacytidine caused a reduced number of cells in the M phase (~15.7% in the control, compared to ~10.6% for 5 μM Aza) and the G1-G0 phase (~72.2% in the control, compared to ~62.6% for 5 μM Aza), associated with an increased number in the S phase (~6.9% in the control, compared to ~13.5% for 5 μM Aza) and the G2 phase (~5.2% in the control, compared to ~13.1% for 5 μM Aza).

TABLE 1

| Percentages of cells in different cell cycle phases | | | | | |
|---|---|---|---|---|---|
| | G1-G0 | G2 | S | M | n |
| U87 | 72.17 ± 1.49 | 5.21 ± 1.12 | 6.92 ± 1.3 | 15.7 ± 1.47 | 15 |
| U87 + Aza | 62.61 ± 0.47 | 13.1 ± 2.36 | 13.54 ± 1.25 | 10.58 ± 2.85 | 15 |
| U87 H-GFP | 65.28 ± 5.98 | 6.26 ± 1.71 | 12.33 ± 5.77 | 15.95 ± 2 | 11 |
| U87 H-GFP + Aza | 61.53 ± 4.06* | 8.77 ± 1.44 | 13.3 ± 3.26* | 16.26 ± 2.83* | 11 |

4) Statistical Analysis

The P values were calculated using the program "Anova, 1-faktorielle-Varianz-Analyse" with MS Excel. The P values <0.05 were regarded as statistically significant.

Table 1 shows the cell cycle analysis: 5-azacytidine influences the cell cycle only in the parent cell line U87 but not in U87H-GFP. The percentages of the cells in the G1-G0, S, G2 and M phases of the cell cycle were obtained as described in FIG. 4.

Apart from an increased number of cells in the G2 phase, U87H-GFP exhibited no significant differences in the cell cycle when treated with 5 µM Aza. In contrast, there were significant changes in the cell cycle phases of U87 when kept in a culture containing 5 µM Aza for 2 days. A reduced number of cells in the G1-G0 and M phases was associated with an increased number in the G2 and S phases.

What is claimed is:

1. A method of determining the effects of a compound on a non-inducible promoter in a eukaryotic cell, comprising:
   a) incubating the eukaryotic cell in a culture medium containing an antibiotic corresponding to an antibiotic resistance gene, wherein said eukaryotic cell comprises a DNA construct, said DNA construct consisting essentially of a fusion gene under the control of the promoter, wherein the promoter is active in said culture medium without any specific requirements for promoter induction, wherein said fusion gene comprises the antibiotic resistance gene and a reporter gene, and wherein activity of the promoter is reduced in the absence of the antibiotic when expression of the resistance gene is not required for growth of the cell;
   b) inoculating a culture medium lacking said antibiotic with the incubated cells from step a);
   c) incubating the culture medium inoculated with the cells from step b) for about 5 hours to about 100 hours, wherein a basal activation level of the promoter in the absence of the antibiotic is achieved;
   d) checking the incubated cells from step c) for expression of the reporter gene to determine an amount of expression of the reporter gene in the absence of said compound;
   e) adding said compound to said culture medium of the cells from step c);
   f) incubating said culture medium with the cells and said compound for about 1 day to about 5 days;
   g) checking the incubated cells from step f) for expression of the reporter gene to determine an amount of expression of the reporter gene in the presence of said compound;
   h) comparing the amount of expression in the presence of said compound with the amount of expression in the absence of said compound from step d), wherein an increase in the amount of expression in the presence of said compound indicates that the compound has an effect on the promoter in said eukaryotic cell.

2. The method of claim 1, wherein said incubating of the culture medium inoculated with the cells in step c) is for about 24 hours.

3. The method of claim 1, wherein said incubating of said culture medium with the cells and said compound in step f) is for about 2 days.

4. The method of claim 1, wherein the DNA construct is in a plasmid.

5. The method of claim 1, wherein the DNA construct is in a virus.

6. The method of claim 1, wherein the promoter is selected from the group consisting of: a Cytomegalovirus (CMV) promoter, a Rous sarcoma virus (RSV) promoter, a cellular promoter of a tumor suppressor gene and a promoter of a differentiation gene.

7. The method of claim 1, wherein the reporter gene is selected from the group consisting of: GFP, LacZ and luciferase.

8. The method of claim 1, wherein the resistance gene is selected from the group consisting of a neomycin resistance gene and a puromycin resistance gene.

9. The method of claim 1, wherein the resistance gene is a hygromycin resistance gene.

10. The method of claim 1, wherein said cell is a human cell.

11. The method of claim 4, wherein said cell is from the cell line U87-HGFP which was deposited in accordance with the Budapest Treaty at the DSMZ in Brunswick, Germany, under deposition number DSMZ ACC 2473 on Nov. 9, 2000.

12. The method of claim 1, wherein the promoter is the human CMV promoter.

13. The method of claim 12, wherein the resistance gene is a hygromycin resistance gene.

* * * * *